United States Patent [19]
Horne et al.

[11] Patent Number: 6,036,680
[45] Date of Patent: *Mar. 14, 2000

[54] SELF-PRIMING SOLUTION LINES AND A METHOD AND SYSTEM FOR USING SAME

[75] Inventors: Peter Horne, Penrith, Australia; Eric J. Hénaut, Arquennes; Patrick Balteau, Ohey, both of Belgium; Michael T. K. Ling, Vernon Hills, Ill.

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/789,109

[22] Filed: Jan. 27, 1997

[51] Int. Cl.[7] .................................................... A61B 19/00
[52] U.S. Cl. ......................... 604/414; 604/413; 604/412
[58] Field of Search .................................. 604/403, 412, 604/413, 414, 415, 905

[56] References Cited

U.S. PATENT DOCUMENTS

| | | |
|---|---|---|
| 2,065,829 | 12/1936 | Schwab . |
| 3,931,818 | 1/1976 | Goldowsky . |
| 4,405,047 | 9/1983 | Barba . |
| 4,787,898 | 11/1988 | Raines ....................................... 604/411 |
| 5,049,129 | 9/1991 | Zdeb et al. ................................ 604/85 |
| 5,358,501 | 10/1994 | Meyer ....................................... 604/414 |
| 5,533,647 | 7/1996 | Long-Hsiung ........................... 604/414 |

FOREIGN PATENT DOCUMENTS

| | | |
|---|---|---|
| 0 001 114 | 3/1979 | European Pat. Off. . |
| 39 01 068 | 8/1989 | Germany . |

*Primary Examiner*—Ronald Stright, Jr.
*Assistant Examiner*—David J. Cho
*Attorney, Agent, or Firm*—Charles R. Mattenson; Paula J. F. Kelly; Robert M. Barrett

[57] ABSTRACT

A system, a method and administration lines are provided for self-priming of a solution delivery system. The administration lines are arranged such that resultant forces acting on the lines create different forces applied on each lumen resulting in solution flowing in one of the lumen undergoing a higher isostatic pressure. The lumens forming the administration line may be formed from concentric tubings or formed from separate tubings extending varied lengths into the solution container. As a result, automatic priming of the administration line and the solution delivery system is provided.

19 Claims, 3 Drawing Sheets

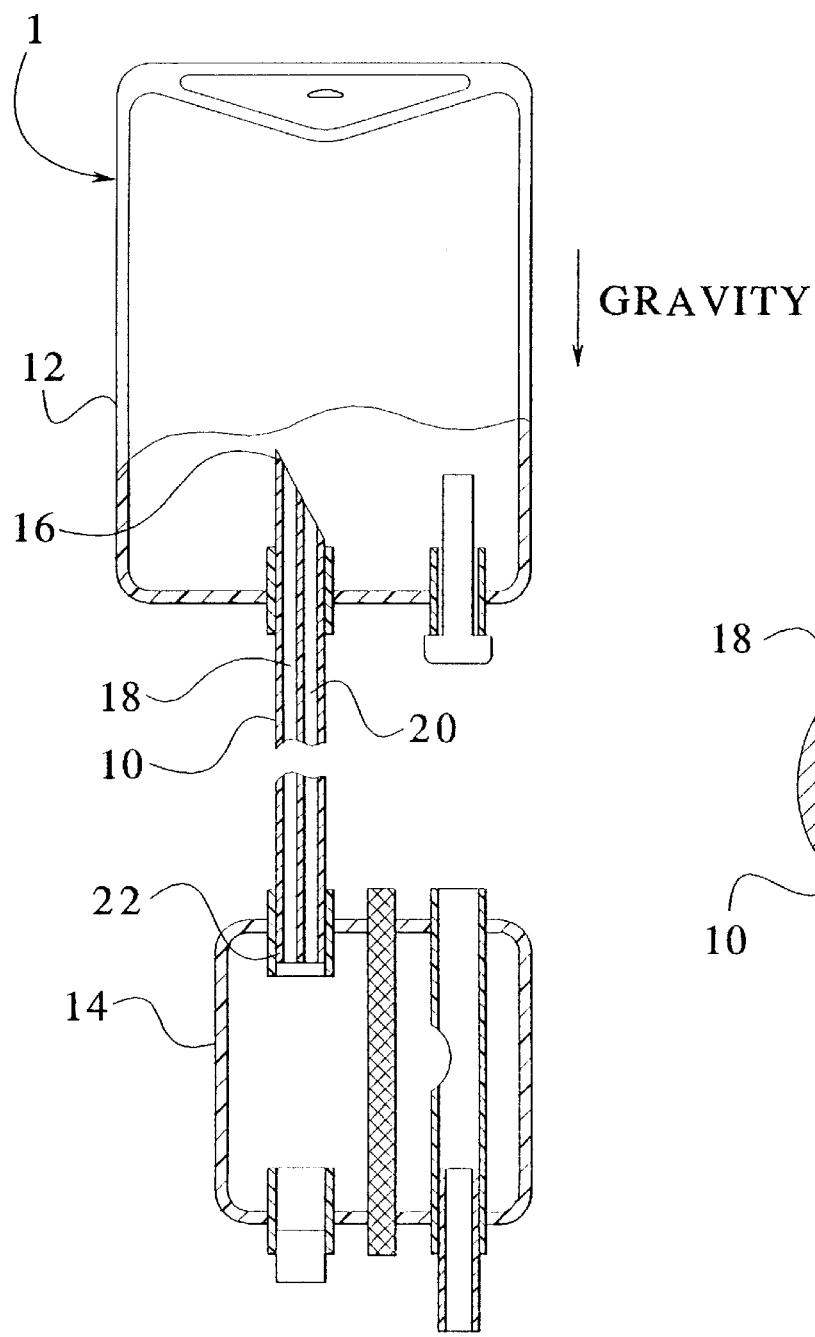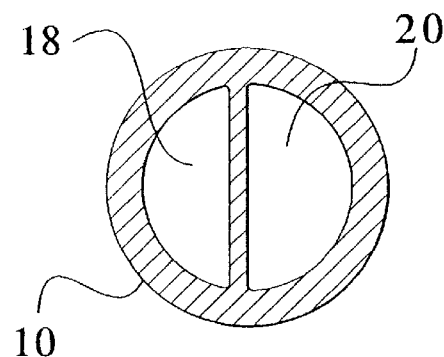

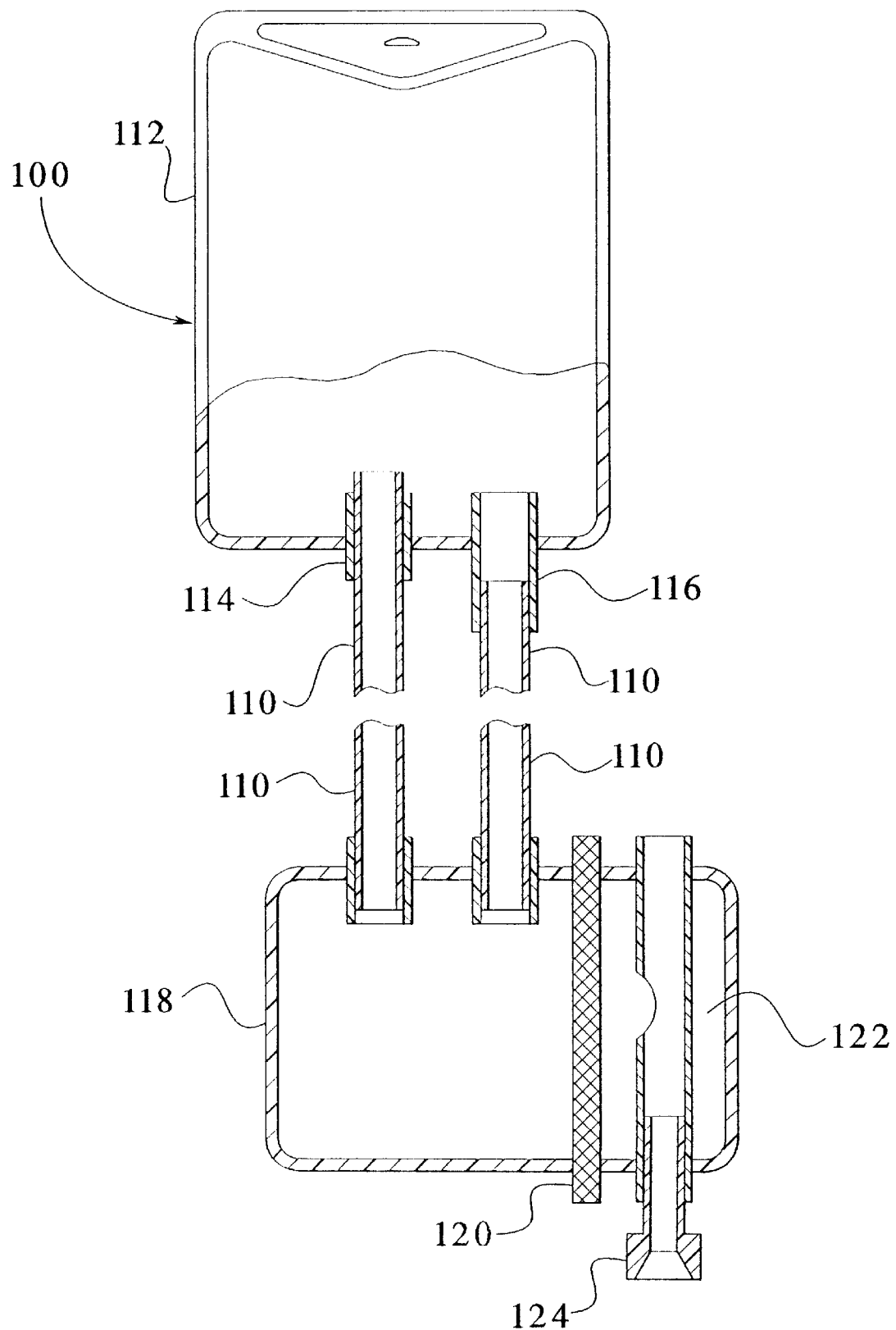

SELF-PRIMING SOLUTION LINES AND A METHOD AND SYSTEM FOR USING SAME

BACKGROUND OF MIE INVENTION

The present invention generally relates to a system and a method for self-priming as well as a solution line used with the system and method. More specifically, the present invention relates to a system and method for self-priming solution lines of a system including a solution container and an attached set that provides fluid communication with the solution container.

It is, of course, generally known to provide a solution container with an attached set or a pre-attached set. The set provides fluid communication between an interior of the solution container and allows transfer of that solution from the interior of the container to a remote location, such as to a patient or to another container.

A typical use of such a container and set is in the field of continuous ambulatory peritoneal dialysis (CAPD). Often a "flush" procedure is performed on the set prior to beginning CAPD. The intent of the "flush" procedure is to prevent infusion of air into the peritoneal cavity by "priming" the administration line with solution; and to serve as a microbial "wash" of each component of the set prior to administration of solution to, for example, a patient.

There are, of course, many products currently available that deliver solutions. Some of the products are delivered without any air or gas in the administration line or lines and/or the container. To manufacture such a product without air or gas, however, special materials are required to be used and/or very heavy manufacturing equipment may be necessary to draw a vacuum before filling.

Generally, when a flexible container is filled with a solution, lines leading to the container are not completely filled with the solution since no way for air or gas exists to be removed since the result of forces, such as surface tensions, weight of column of water and gravity, applied on a given volume equals zero inside the administration line, i.e. equilibrium exists. Therefore, unless special materials and/or heavy manufacturing equipment is implemented to draw a vacuum before filling, air or gas is likely to exist in the administration lines and/or tie container.

A need, therefore, exists for an improved system, method and administration line that overcome the deficiencies of prior known systems by providing a simplified arrangement for self-priming.

SUMMARY OF THE INVENTION

The present invention provides a system, a method and an administration line for self-priming a fluid delivery system are provided. The system performs self-priming of the fluid delivery system due to specifically designed administration lines that create a difference between the forces applied on each lumen of the administration line to result in a higher isostatic pressure to one of the lumens of the administration line.

To this end, in an embodiment, a system is provided for self priming a fluid delivery system. The system has a container having an interior holding a solution. A chamber is remotely situated downstream from the container having an interior. A first lumen in fluid communication with the solution of the interior of the container is provided wherein a first end of the first lumen extends into the interior of the container and a second end of the first lumen extends into the chamber. A second lumen is provided in fluid communication with the solution of the interior of the container wherein a first end of the second lumen extends into the container a distance greater than the first end of the first lumen and a second end of the second lumen extends into the chamber.

In an embodiment, the first lumen and the second lumen are integrally formed having a common wall separating the first lumen from the second lumen.

In an embodiment, the second lumen is concentrically located within the first lumen.

In an embodiment, the first lumen and the second lumen share a common wall and are non-symmetrical with respect to the wall.

In an embodiment, the first lumen is remotely situated from the second lumen.

In an embodiment, the system has a first port to which the first lumen is attached and a second port to which the second lumen is attached wherein the second port extends from the container a distance greater than the first port.

In an embodiment, the first lumen and the second lumen are integrally formed and a first end of each of the lumens are beveled to form an angled tip in the interior of the container.

In an embodiment, a clamp is provided to separate the chamber into two areas.

In another embodiment of the present invention, an administration line is provided for connecting between a container having an interior holding a solution and a chamber having an interior. The administration line has a first lumen having a first end and a second end wherein the first end extends into the interior of the container and a second end extends into the interior of the chamber to provide fluid communication between the container and the chamber. A second lumen has a first end and a second end wherein the first end of the second lumen extends into the container a distance greater than the first end of the first lumen and the second end extends into the interior of the chamber to provide fluid communication between the container and the chamber.

In an embodiment, the first lumen and the second lumen are integrally formed.

In an embodiment, the first lumen and the second lumen are remotely situated.

In an embodiment, the first lumen and the second lumen are concentrically arranged with the second lumen extending through the first lumen.

In an embodiment, the first lumen and the second lumen share a common wall and are non-symmetrical with respect to the wall.

In an embodiment, the first lumen and the second lumen are integrally formed and the first end of each of the lumens are beveled to form an angled tip in the interior of the container.

In another embodiment of the present invention, a method is provided for self-priming of a fluid delivery system, the method comprises the steps of: providing a container having an interior holding a solution; providing a first lumen in fluid communication with the solution in the interior of the container; and providing a second lumen in fluid communication with the solution in the interior of the container wherein the second lumen extends into the interior of the container a distance greater than the first lumen extends into the interior of the first container.

In an embodiment, the method further comprises the step of: providing a chamber in fluid communication with the first lumen and the second lumen wherein the chamber is situated remotely from the container such that the solution from the container flows through the first lumen and the second lumen to the chamber.

In an embodiment, the first lumen and the second lumen are integrally formed.

In an embodiment, the first lumen and the second lumen are remotely situated.

In an embodiment, the first lumen and the second lumen share a common wall and are non-symmetrical with respect to the wall.

In an embodiment, the first lumen and the second lumen are concentrically arranged with the second lumen extending through the first lumen.

It is, therefore, an advantage of the present invention to provide a system and a method for self-priming a delivery system and an administration line for use with such system which results in simplified self-priming of the delivery system.

Yet another advantage of the present invention is to provide a system, a method and an administration line for quickly self-priming a delivery system.

Yet another advantage of the present invention is to provide a system, a method and an administration line for economically self-priming a delivery system.

A still further advantage of the present invention is to provide a system, a method and an administration line for self-priming of a delivery system without requiring special materials to perform the same.

Moreover, an advantage of the present invention is to provide a system, a method and an administration line for self-priming a delivery system without requiring any sophisticated manufacturing equipment.

Additional features and advantages of the present invention are described in, and will be apparent from, the detailed description of the presently preferred embodiments and from the drawings.

BRIEF DESCRIPTION OF THE DRAWINGS

FIG. 1 illustrates a plan view, partially in cross-sectional detail, of an embodiment of a solution container and attached set of the present invention.

FIG. 2 illustrates a cross-sectional view of an embodiment of an administration line of the present invention.

FIG. 3 illustrates a plan view, partially in cross-sectional detail, of an embodiment of a solution container and attached set of the present invention.

DETAILED DESCRIPTION OF THE PRESENTLY PREFERRED EMBODIMENTS

Figure 4:
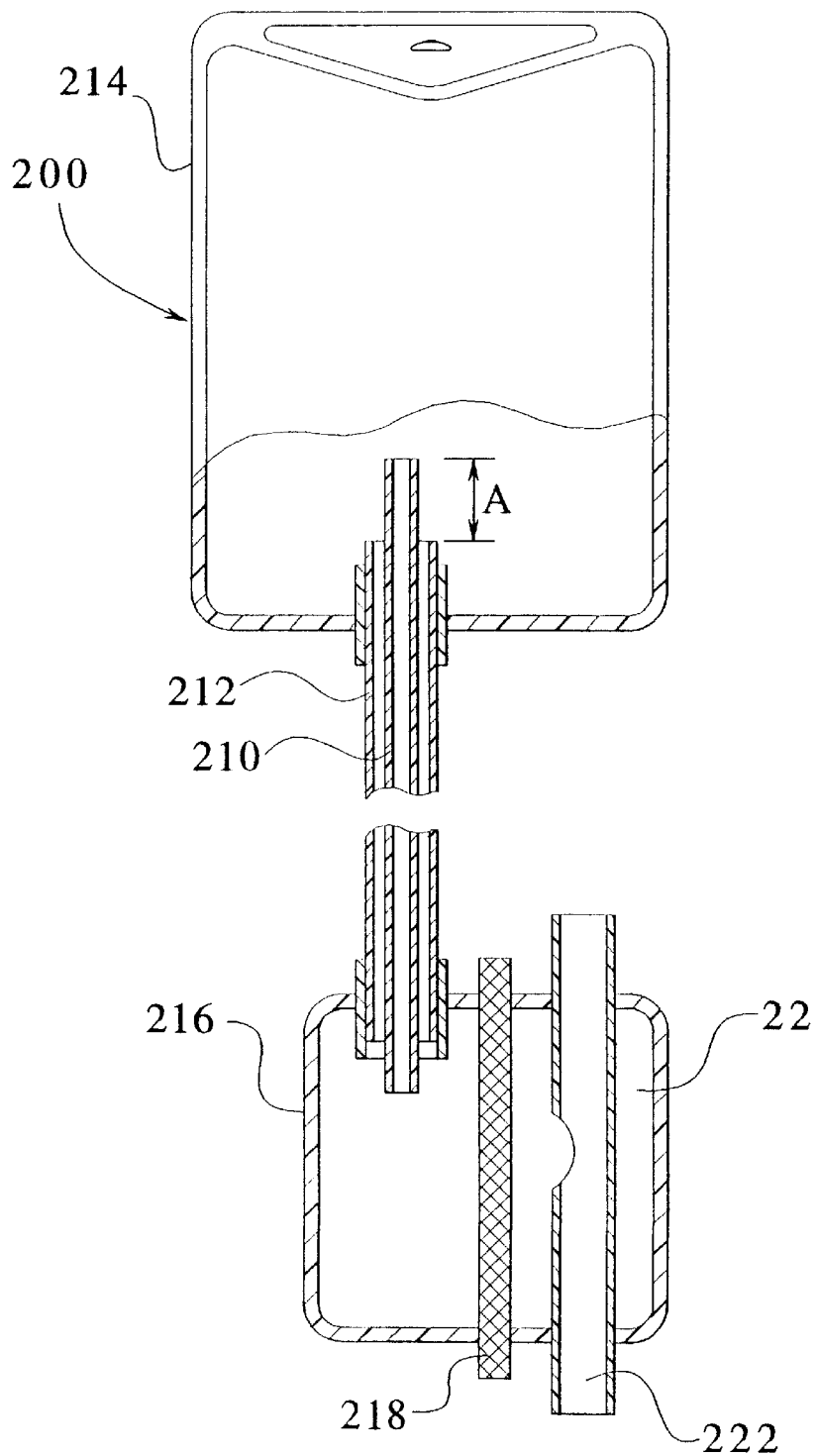
FIG. 4 illustrates a plan view, partially in cross-sectional detail, of another embodiment of a solution bag and set of the present invention.

The present invention provides a system and a method for self-priming of a solution line or lines. More specifically, the present invention provides a system and a method for self-priming a solution line from a container having solution therein, the line being a part of an attached set that provides fluid communication between the interior of the container and the set.

Referring now to the drawings wherein like numerals refer to like parts, FIG. 1 illustrates an embodiment of a system 1 that provides self-priming of an administration line 10. The administration line 10 is connected to a solution container 12 at a first end and to a second solution container or chamber 14 at an opposite end of the administration line 10. A first end 16 of the administration line 10 is configured such that, when the solution container 12 is hanging in a vertical position, the solution in the container 10 exerts a different isostatic pressure on each lumen 18,20 of the administration line 10.

The chamber 14 is connected to a second end 22 of the administration line 10 and allows for closing of the loop provided by the dual lumens 18,20. As a result, self-priming of the administration line 10 occurs. The dual lumens 18,20 formed in the administration line 10 are constructed from a material that reduces surface tensions to avoid a drop of liquid or gas to be entrapped within the lumens 18,20. In a preferred embodiment, the administration line 10 and the dual lumens 18,20 are constructed from a polymeric material, preferably polyvinyl chloride or polyolefin material such as metallocene polyethylene with a density range from 0.87 to 0.91 grams per cubic centimeters, amorphous or low crystallinity polypropylene with a Young's Modulus of 3,000 to 20,000 pounds per square inch, ethylene vinyl acetate, ethylene methylacrylate, S-EB-S (styrene-ethylene butadiene-styrene), thermoplastic styrenic elastomer, etc., or a combination thereof.

The lines and multi-lumen tubing can be made from a single ingredient or by blending two or more of the aforementioned ingredients. Moreover, said tubing can be obtained by extrusion or co-extrusion of one or more ingredients into a single layer or multi-layer tubing.

When the container 12 is filled with solutions, the administration line 10 connected to the container 12 is not completely filled with solution since no way exists for air or gas to be removed from the container since the resultant forces dues to surface tensions, weight of column of solution and gravity applied on a given volume is zero, i.e. at equilibrium, inside the administration line 10. However, when the administration line 10 includes a loop formed by the dual lumens 18,20, a difference is created between the forces applied on one of the lumens of the administration line 10 due to the proper design of the administration line 10.

Namely, when the container 12 is hanging, solution flows in the lumen which undergoes a higher isostatic pressure. A bolus of the solution pushes through the loop formed by the lumens 18,20, forcing the air or gas volume back into the container 12. The motion created by the volume of air or gas maintains the dynamics of the solution as it forces the volume of liquid. As a result, both lumens 18,20 of the administration line 10 are completely filled with solution as a result of gravity forcing solution from the container 12 into the administration line 10 thereby initiating the process of self-priming.

As illustrated in FIG. 1, the administration line 10 is constructed from dual lumens 18,20 that may be individual sections of single lumen tubing materialized into a dual lumen tubing.

FIG. 2 illustrates a cross-sectional view of the administration line 10 and the dual lumens 18,20. The lumens 18,20 are non-symmetrical to reinforce the difference in surface tensions already generated by the bevel formed at the first end 16 of the administration line 10. Self-priming of the administration line 10 through the dual lumens 18,20 occurs as a result of the bevel formed at the first end 16 of the administration line 10. The non-symmetrical arrangement of the lumen 18,20, as illustrated, in FIG. 2 further enhances the self-priming.

Another embodiment of a system 100 for self-priming of administration lines 110 is illustrated in FIG. 3. As shown, the system 100 has a pair of administration lines 110 connected to a solution container 112. Port tubes 114,116 of different lengths are provided to create a difference in forces applied on each of the single lumen administration lines 110. Like the system 1 illustrated with reference to FIG. 1, the administration lines 110 are attached to a chamber 118 which may be closed by a clamp 120. An area 122 of the chamber 118 is thereby sectioned from the remainder of the chamber 118 and is terminated by a connector 124. Of course, other embodiments of the chamber 118 may be implemented for the particular application in which self-priming of the administration lines 110 is required. As a result of the unique arrangement of the administration line 110 and their positioning with respect to an interior of the solution container 112 by the ports 114 and 116, the administrations lines 110 may be completely self-primed following connection.

Figure 5:
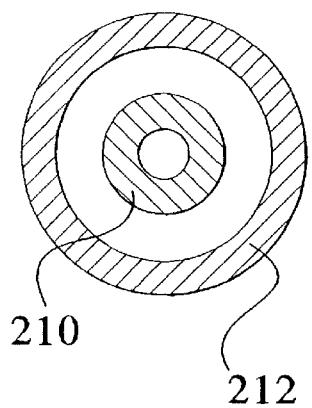
FIG. 5 illustrates a cross-sectional view of an embodiment of a dual lumen administration line of the present invention.

Referring now to FIGS. 4 and 5, another embodiment of an administration line creating a system 200 for self-priming thereof is shown. The system 200 includes a single smaller lumen 210 within a larger lumen 212. The lumens 210,212 are in fluid communication with a solution container 214. The lumen 210 is fitted to the solution container 214 such that it extends into the interior of the container 214 a distance A beyond the lumen 212. As a result, a difference in forces is created by this arrangement activating the process of self-priming of the administration lines formed by the lumens 210,212. A cross-sectional view of the smaller lumen 210 and the larger lumen 212 is shown in FIG. 5. As previously described with reference to FIGS. 1 and 3, the lumens 210,212 may be in fluid communication with a second chamber 216. As also previously described, the second chamber 216 nay be divided by a clamp 218 creating a smaller area 220 in which a port 222 is separately accessible.

Although the present invention has been described for applications involving peritoneal dialysis ill which a flexible solution container contains a solution for delivery thereof thorough administration lines, the present invention may also be applied to any other system that requires priming of its administration lines prior to usage, such as drug delivery systems, IV solution systems and the like.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for self-priming a fluid delivery system, the system comprising:

a container having an interior holding a solution;

a chamber having an interior;

a first lumen in fluid communication with the solution in the interior of the container wherein a first end of the first lumen extends into the interior of the container and into the solution and a second end of the first lumen extends into the interior of the chamber, the first end of the first lumen having a first cross sectional area; and a second lumen in fluid communication with the solution in the interior of the container wherein a first end of the second lumen extends into the container and into the solution a distance greater than the first end of the first lumen, a second end of the second lumen extends into the interior of the chamber, the first end of the second lumen having a second cross sectional area, the second cross sectional area being less than the first cross sectional area, wherein when the container is disposed vertically above the chamber, both the first and second lumens and the chamber will be primed with the solution and any gas disposed in the first and second lumens and the chamber will be forced upward through the second lumen into the container.

2. The system of claim 1 wherein the first lumen and the second lumen are integrally formed having a common wall separating the first lumen from the second lumen.

3. The system of claim 1 wherein the second lumen is concentrically located within the first lumen.

4. The system of claim 1 wherein the first lumen and the second lumen share a common wall and are non-symmetrical with respect to the wall.

5. The system of claim 1 wherein the first lumen is remotely situated from the second lumen.

6. The system of claim 1 further comprising:

a first port to which the first lumen is attached; and a second port to which the second lumen is attached wherein the second port extends from the container a distance greater than the first port.

7. The system of claim 1 wherein the first lumen and the second lumen are integrally formed and the first end of each of the lumens are beveled to form an angled tip in the interior of the container.

8. The system of claim 1 further comprising:

a clamp separating the chamber into two areas.

9. An administration line for connecting between a container having an interior holding a solution and a chamber having an interior, the administration line comprising:

a first lumen having a first end and a second end wherein the first end extends into the interior of the container and into the solution and the second end extends into the interior of the chamber to provide fluid communication between the container and the chamber, the first end of the first lumen having a first cross sectional area; and a second lumen having a first end and a second end wherein the first end of the second lumen extends into the container and into the solution a distance greater than the first end of the first lumen, the second end extends into the interior of the chamber to provide fluid communication between the container and the chamber, the first end of the second lumen having a second cross sectional area, the second cross sectional area being less than the first cross sectional area, wherein when the container is disposed vertically above the chamber, both the first and second lumens and the chamber will be primed with the solution and any gas disposed in the first and second lumens and the chamber will be forced upward through the second lumen into the container.

10. The administration line of claim 9 wherein the first lumen and the second lumen are integrally formed.

11. The administration line of claim 9 wherein the first lumen and the second lumen are remotely situated.

12. The administration line of claim 9 wherein the first lumen and the second lumen are concentrically arranged with the second lumen extending through the first lumen.

13. The administration line of claim 9 wherein the first lumen and the second lumen share a common wall and are non-symmetrical with respect to the wall.

14. The administration line of claim 9 wherein the first lumen and the second lumen are integrally formed and the first end of each of the lumens are beveled to form an angled tip in the interior of the container.

15. A method for self-priming of a fluid delivery system, the method comprising the steps of:

providing a container having an interior holding a solution;

providing a first lumen having a first end in fluid communication with the solution in the interior of the container; and providing a second lumen having a first end in fluid communication with the solution in the interior of the container wherein the first end of the second lumen extends into the interior of the container and into the solution a distance greater than the first end of the first lumen extends into the interior of the container and into the solution, the first end of the first lumen having a first cross sectional area, the first end of the second lumen having a second cross sectional area, the second cross sectional area being less than the first cross sectional area;

providing a chamber in fluid communication with the first lumen and the second lumen wherein the chamber is situated remotely from and vertically below the container such that solution from the container flows through the first lumen and the second lumen to the chamber and air or gas flows from the chamber and first and second lumens through the second lumen and into tire container.

16. The method of claim 15 wherein the first lumen and the second lumen are integrally formed.

17. The method of claim 15 wherein the first lumen and the second lumen are remotely situated.

18. The method of claim 15 wherein the first lumen and the second lumen share a common wall and are nonsymmetrical with respect to the wall.

19. The method of claim 15 wherein the first lumen and the second lumen are concentrically arranged with the second lumen extending through the first lumen.

* * * * *